United States Patent
Jadaun et al.

(10) Patent No.: US 11,898,105 B2
(45) Date of Patent: Feb. 13, 2024

(54) PROCESS FOR PRODUCING RENEWABLE PRODUCT STREAMS

(71) Applicant: UOP LLC, Des Plaines, IL (US)

(72) Inventors: Krishan Pratap Jadaun, Gurugram (IN); Andrea G. Bozzano, Northbrook, IL (US); Krishna Mani, Gurgaon (IN); Stanley Joseph Frey, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 17/513,651

(22) Filed: Oct. 28, 2021

(65) Prior Publication Data
US 2023/0137687 A1    May 4, 2023

(51) Int. Cl.
| | | |
|---|---|---|
| *C10G 3/00* | (2006.01) | |
| *C07C 1/24* | (2006.01) | |
| *C07C 2/64* | (2006.01) | |
| *C07C 15/107* | (2006.01) | |
| *C07C 2/76* | (2006.01) | |
| *C10G 45/58* | (2006.01) | |
| *C10G 45/02* | (2006.01) | |

(52) U.S. Cl.
CPC .............. *C10G 3/50* (2013.01); *C07C 2/64* (2013.01); *C07C 2/76* (2013.01); *C07C 15/107* (2013.01); *C10G 3/42* (2013.01); *C10G 45/02* (2013.01); *C10G 45/58* (2013.01); *C10G 2300/1014* (2013.01); *C10G 2300/1051* (2013.01); *C10G 2400/04* (2013.01); *C10G 2400/08* (2013.01); *C10G 2400/30* (2013.01)

(58) Field of Classification Search
CPC . C10G 3/42; C10G 3/50; C10G 45/02; C10G 45/58; C10G 2300/1014; C10G 2300/1051; C10G 2400/04; C10G 2400/08; C10G 2400/30; C07C 2/64; C07C 2/76; C07C 15/107
See application file for complete search history.

(56) References Cited

U.S. PATENT DOCUMENTS

| | | | |
|---|---|---|---|
| 8,853,479 B2 * | 10/2014 | Bozzano | C07C 2/68 585/314 |
| 9,079,811 B2 | 7/2015 | Frey et al. | |
| 9,080,134 B2 | 7/2015 | Frey | |

(Continued)

OTHER PUBLICATIONS

Search Report and Written Opinion for PCT/US2022/078507 dated Feb. 24, 2023.

*Primary Examiner* — Youngsul Jeong
*Assistant Examiner* — Jason Y Chong
(74) *Attorney, Agent, or Firm* — Paschall & Associates, LLC; James C. Paschall

(57) ABSTRACT

Hydrodeoxygenating a biorenewable feed that is concentrated in free fatty acids with 10-13 carbon atoms at a moderate hydrodeoxygenation ratio that is less than the ratio of hydrodeoxygenation utilized for traditional biorenewable feeds such as vegetable oil or even mineral feedstocks, normal paraffins in the range desired by the detergents industry can be produced. Either hydroisomerization or an iso-normal separation can be performed to provide green fuel streams. Two reactors are proposed, one for hydrodeoxygenation of the biorenewable feed that is concentrated in free fatty acids with 10-13 carbon atoms and the other for a traditional biorenewable feed or even a mineral feed operated at a higher deoxygenation ratio.

10 Claims, 3 Drawing Sheets

(56) References Cited

U.S. PATENT DOCUMENTS

| | | |
|---|---|---|
| 2013/0012745 A1 | 1/2013 | Knuuttila et al. |
| 2013/0012746 A1* | 1/2013 | Luebke .................... C10G 3/50 585/251 |
| 2015/0068109 A1 | 3/2015 | Baldiraghi et al. |
| 2015/0240187 A1* | 8/2015 | Scheibel ............... C07C 303/14 510/498 |
| 2015/0266796 A1 | 9/2015 | Chen et al. |
| 2022/0411702 A1 | 12/2022 | Sarjovaara et al. |

* cited by examiner

PROCESS FOR PRODUCING RENEWABLE PRODUCT STREAMS

FIELD

The field is processes for producing product streams from renewable feed streams. Specifically, the field is processes for producing detergent streams and fuel streams from renewable feed streams.

BACKGROUND

Linear alkylbenzenes are organic compounds with the formula $C_6H_5C_nH_{2n+1}$. While the alkyl carbon number, "n" can have any practical value, detergent manufacturers desire that alkylbenzenes have alkyl carbon number in the range of 9 to 16 and preferably in the range of 10 to 13. These specific ranges are often required when the alkylbenzenes are used as intermediates in the production of surfactants for detergents. The alkyl carbon number in the range of 10 to 13 falls in line with the specifications of the detergents industry.

Because the surfactants created from alkylbenzenes are biodegradable, the production of alkylbenzenes has grown rapidly since their initial uses in detergent production in the 1960s. The linearity of the paraffin chain in the alkylbenzenes is key to the material's biodegradability and effectiveness as a detergent. A major factor in the final linearity of the alkylbenzenes is the linearity of the paraffin component.

While detergents made utilizing alkylbenzene-based surfactants are biodegradable, processes for creating alkylbenzenes are not based on renewable sources. Specifically, alkylbenzenes are currently produced from kerosene refined from crude extracted from the earth. Due to the growing environmental prejudice against fossil fuel extraction and economic concerns over exhausting fossil fuel deposits, there may be support for using an alternate source for biodegradable surfactants in detergents and in other industries.

Accordingly, it is desirable to provide linear alkylbenzenes with a high degree of linearity and made from biorenewable sources that are not extracted from the earth. Further, it is desirable to provide renewable linear alkylbenzenes from easily processed triglycerides and fatty acids from vegetable, animal, nut, and/or seed oils. Palm kernel oil, coconut oil and babassu oil have a composition that aligns with the alkyl carbon number range desired of the detergent industry.

Biofuels may be co-produced with the linear alkylbenzenes. Other desirable features and characteristics of the present invention will become apparent from the subsequent detailed description of the invention and the appended claims, when taken in conjunction with the accompanying drawing and this background.

BRIEF SUMMARY

We have discovered that biorenewable feeds that are concentrated in free fatty acids with 10-13 carbon atoms are converted to paraffin compositions favored in detergent alkylation by a moderate hydrodeoxygenation ratio which is less than the ratio of hydrodeoxygenation utilized for traditional biorenewable feeds such as vegetable oil. The disclosure proposes two reactors, one for hydrodeoxygenation of the biorenewable feed that is concentrated in free fatty acids with 12 and 14 carbon atoms and the other for a traditional biorenewable feed or even a mineral feed operated at a higher deoxygenation ratio.

Additional details and embodiments of the disclosure will become apparent from the following detailed description of the disclosure.

DETAILED DESCRIPTION

Figure 1:
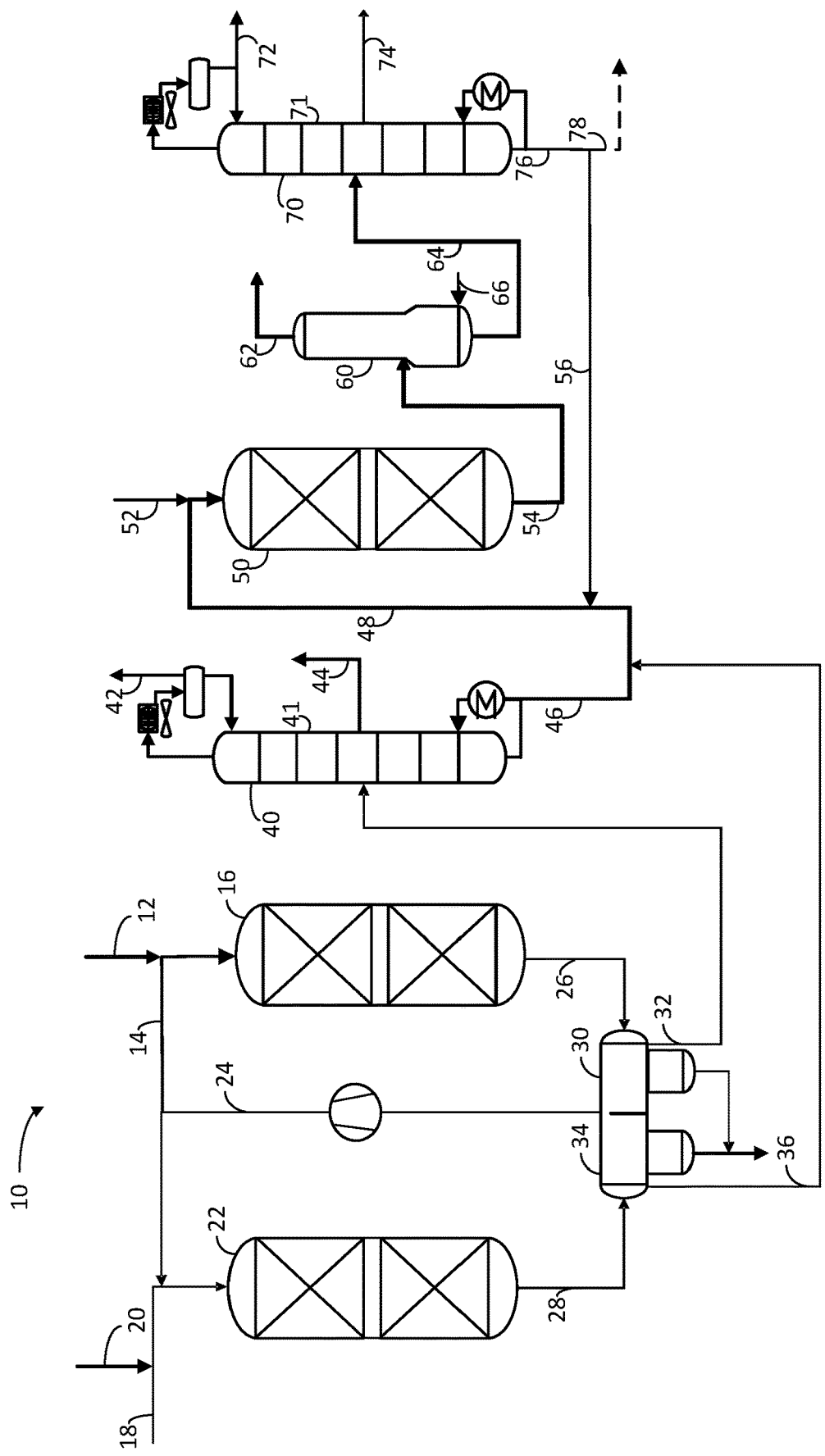
FIG. 1 is a schematic view of a conversion unit of the present disclosure.

The present disclosure endeavors to produce alkylbenzenes for detergent production and jet fuel and/or diesel from renewable sources. Many vegetable oils have fatty acids that when hydrodeoxygenated produce normal paraffins with 16 to 18 carbons which are longer than desired by detergent producers. However, some renewable sources such as palm kernel oil (PKO), coconut oil and babassu oil have fatty acids that produce normal paraffins with 10 to 13 carbons when deoxygenated. Normal paraffins with 10 to 13 carbons are the desired number of carbons that detergent producers desire for the alkyl group on the alkylbenzenes used in detergents.

We have found that the degree of hydrodeoxygenation can affect the selectivity to each of the normal paraffins in the 10 to 13 carbon range. For biorenewable feeds that have fatty acids with 12 and 14 carbon atoms, hydrodeoxygenation converts to normal paraffins with a corresponding number of 12 and 14 carbons atoms, respectively. For example, hydrodeoxygenation of a tryglyceride with fatty acids of 14 carbons atoms produces tetradecane:

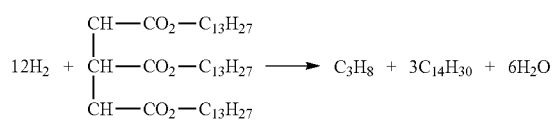

However, decarboxylation or decarbonylation converts fatty acids with 12 and 14 carbon atoms to normal paraffins with one less carbon atom than in the fatty acid having 11 and 13 carbon atoms. For example, decarboxylation of the tryglyceride with fatty acids of 14 carbon atoms produces tridecane and carbon dioxide:

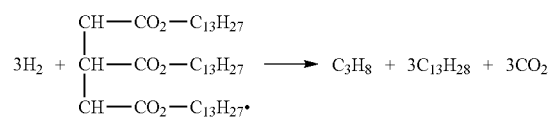

A large degree of hydrodeoxygenation can bias the hydrodeoxygenated composition largely in favor of normal tetradecane and normal dodecane to the detriment of normal tridecane and normal undecane. A small degree of hydrodeoxygenation can bias the hydrodeoxygenated composition in favor of normal tridecane and normal undecane to the detriment of normal tetradecane and normal dodecane. The hydrodeoxygenation ratio is determined by the formula:

$$\text{Hydrodeoxygenation ratio} = \frac{\text{mass flow rate of normal paraffins with even carbon number in product}}{\text{mass flow rate of normal paraffins in product}}$$

We have found that hydrodeoxygenation in terms of percentage between 35 and 60%, preferably 40 and 55%, provides a hydrodeoxygenated composition with normal undecane, normal dodecane and normal tridecane in the range desired by the detergent specifications at least for those n-paraffins. Normal decane has been low in cases and may need to be supplemented to meet detergent specifications.

Other vegetable oils that have fatty acids with carbon numbers in the range of 15 to 20 carbons are typically subjected to a high degree of hydrodeoxygenation to obtain paraffins in the jet fuel or diesel range. The high degree of hydrodeoxygenation is not commensurate with the moderate degree of hydrodeoxygenation of PKO, coconut oil and babassu oil best for detergent production. Hence, we propose to decouple the hydrodeoxygenation of other feed streams from the hydrodeoxygenation of biorenewable streams that produce normal paraffins of 10 to 13 carbons, particularly 11 to 13 carbons, such as PKO, coconut oil and babassu oil, to achieve greater yield of a hydrodeoxygenated composition that is desired in detergents production.

In FIG. 1, we propose decoupling of the hydrodeoxygenation of a, biorenewable feed stream with large amounts of fatty acids with 12 and 14 carbons from hydrodeoxygenation of another biorenewable feed stream with large amounts of fatty acids with 14-20 carbons by utilizing two hydrodeoxygenation reactors.

In accordance with an exemplary embodiment, a process 10 is shown for processing a biorenewable feed stream. A first feed line 12 may transport a first biorenewable feed stream. The term "biorenewable feed stream" is meant to include feedstocks other than those obtained from crude oil. The biorenewable feed stream may include any of those feedstocks which comprise at least one of glycerides and free fatty acids. Most of glycerides will be triglycerides, but monoglycerides and diglycerides may be present and processed as well. Free fatty acids may be obtained from phospholipids which may be a source of phosphorous in the feedstock. The first biorenewable feed stream in line 12 may comprise a biological oil substantially concentrated in free fatty acids having 12 and 14 carbon atoms. The free fatty acids may depend from a glycerine bridge. As used herein, the term "substantial", "substantially", or "substantiate" means greater than 30%, suitably greater than 40% and preferably greater than 50%.

Examples of such biorenewable oils include PKO, coconut oil and babassu oil. The biorenewable feedstock may be pretreated to remove contaminants and filtered to remove solids. The biorenewable feed stream in line 12 may be combined with hydrogen from line 14, heated and fed to a first hydrodeoxygenation reactor 16.

A second feed line 18 transports a second feed stream. The second feed stream in line 18 may comprise a second biorenewable feed stream of biological oil that comprises free fatty acids having 10 to 20 carbon atoms depending from a glycerine bridge. The second feed stream may be a conventional biorenewable oil such as a vegetable oil that is not concentrated in free fatty acids having 12 or 14 carbon atoms. The second feed stream in line 18 may comprise a biological oil substantially concentrated in free fatty acids not having 12 or 14 carbon atoms. A variety of different biorenewable feedstocks may be suitable for the second biorenewable feed stream in the second feed line 18. Examples of these biorenewable feedstocks include, but are not limited to, camelina oil, canola oil, corn oil, soy oil, rapeseed oil, soybean oil, colza oil, tall oil, sunflower oil, hempseed oil, olive oil, linseed oil, castor oil, peanut oil, mustard oil, tallow, yellow and brown greases, lard, train oil, fats in milk, fish oil, algal oil, sewage sludge, and the like. Additional examples of biorenewable feedstocks include non-edible vegetable oils from the group comprising Jatropha curcas (Ratanjot, Wild Castor, Jangli Erandi), Madhuca indica (Mohuwa), Pongamia pinnata (Karanji, Honge), calophyllum inophyllum, moringa oleifera and Azadirachta indica (Neem). The triglycerides and FFAs of the typical vegetable or animal fat contain aliphatic hydrocarbon chains in their structure which have about 8 to about 30 carbon atoms. As will be appreciated, the biorenewable feedstock may comprise a mixture of one or more of the foregoing examples. The second feed stream in line 18 may be combined with hydrogen from line 20, heated and fed to a hydrotreating reactor 22.

The first hydrodeoxygenation reactor 16 may comprise beds of hydrodeoxygenation catalyst for hydrodeoxygenating the first biorenewable feed stream in the presence of hydrogen to hydrodeoxygenate the first biorenewable feed stream to provide a first hydrodeoxygenated stream. The hydrotreating reactor 22 may comprise beds of hydrotreating catalyst for hydrotreating the second feed stream in the presence of hydrogen to hydrotreat the second feed stream to provide a hydrotreated stream. In the embodiment of FIG. 1 the hydrotreating reactor may comprise a second hydrodeoxygenation reactor 22 comprising beds of hydrodeoxygenation catalyst for hydrodeoxygenating the second biorenewable feed stream in the presence of hydrogen to hydrodeoxygenate the second biorenewable feed stream to provide a second hydrodeoxygenated stream.

The hydrodeoxygenation reactions occurring in the hydrodeoxygenation reactors 16, 22 include hydrodecarbonylation and hydrodecarboxylation reactions. Additionally, other hydrotreating reactions occur in the hydrodeoxygenation reactors 16, 22 including olefin saturation, hydrodemetallation, which removes phosphorous, hydrodesulfurization and hydrodenitrification.

Conditions in the first hydrodeoxygenation reactor 16 may include a temperature of about 250° C. (482° F.) to about 400° C. (752° F.) and a pressure of about 700 kPa (abs) (100 psig) to about 21 MPa (abs) (3000 psig). The hydrodeoxygenation reactor temperatures may be kept low, less than 343° C. (650° F.) for typical biorenewable feedstocks and less than 304° C. (580° F.) for feedstocks with higher free fatty acid (FFA) concentration to avoid polymerization of olefins found in FFA. Generally, hydrodeoxygenation reactor pressure of about 1.9 MPa (abs) (285 psia) to about 14.7 MPa (abs) (2133 psia) are suitable.

The first hydrodeoxygenation reactor 16 and the second hydrotreating reactor 22 may include guard bed catalyst comprising a base metal on a support. Base metals useable in this process include nickel, chromium, molybdenum and tungsten. Other base metals that can be used include tin, indium, germanium, lead, cobalt, gallium and zinc. The base metals are active in the sulfide form. In a further embodiment, the guard bed catalyst can comprise a second metal, wherein the second metal includes one or more of the metals: tin, indium, ruthenium, rhodium, rhenium, osmium, iridium, germanium, lead, cobalt, gallium, zinc and thallium. A nickel molybdenum on alumina catalyst may be a suitable catalyst in the guard bed. A hydrogen quench stream may be injected at spaced or interbed locations to control temperature exotherms.

The first hydrodeoxygenation reactor 16 and the second hydrotreating reactor 22 may also include a bed of hydrodeoxygenation catalyst to further hydrodemetallate, hydrodeoxygenate, including hydrodecarbonylate and hydrodecarboxylate, hydrodenitrogenate and hydrodesulfurize the respective feed stream. Metals removed include alkali metals and alkali earth metals and phosphorous. Olefinic or unsaturated portions of the n-paraffinic chains in the biorenewable feedstock are also saturated. Hydrodeoxygenation reactions including hydrodecarboxylation and hydrocarbonylation reactions to remove oxygenate functional groups from the biorenewable feedstock molecules which are converted to water and carbon oxides. The hydrodeoxygenation catalyst also catalyzes desulfurization of organic sulfur and denitrogenation of organic nitrogen in the biorenewable feed stream.

The hydrodeoxygenation catalyst may comprise nickel, nickel/molybdenum, or cobalt/molybdenum dispersed on a high surface area support such as alumina. Suitable hydrotreating catalysts include BDO 200 or BDO 300 available from UOP LLC in Des Plaines, Illinois. The hydrodeoxygenation catalyst should be in sulfided form. Hydrogen sulfide from a recycle hydrogen stream in line 24 may provide sulfur for catalyst sulfidation.

The first hydrodeoxygenation reactor 16 produces a hydrodeoxygenated stream in line 26. The hydrodeoxygenated stream comprises a hydrocarbon fraction which has a substantial n-paraffin concentration in the 10 to 13 carbon atom range, preferably in the 11 to 13 carbon atom range. Oxygenate concentration in the hydrocarbon fraction is essentially nil, whereas the olefin concentration is substantially reduced relative to the first biorenewable feed stream. The organic sulfur concentration in the hydrocarbon fraction may be no more than 500 wppm and the organic nitrogen concentration in the hydrocarbon fraction may be less than 10 wppm. Conditions in the first hydrodeoxygenation reactor 16 are operated so as to achieve a hydrodeoxygenation ratio of about 35 to about 60% and preferably about 40 to about 55%.

The second hydrotreating reactor 22 produces a hydrotreated stream in line 28. The hydrotreated stream may be a second hydrodeoxygenated stream in line 28 in which case the hydrodeoxygenated stream in line 26 is a first hydrodeoxygenated stream. The hydrotreated stream comprises a hydrocarbon fraction which has a substantial n-paraffin concentration in the 14 to 20 carbon atom range. Oxygenate concentration in the hydrocarbon fraction is essentially nil, whereas the olefin concentration is substantially reduced relative to the first biorenewable feed stream. The organic sulfur concentration in the hydrocarbon fraction may be no more than 500 wppm and the organic nitrogen concentration in the hydrocarbon fraction may be less than 10 wppm. Conditions in the hydrotreating reactor 22 may include a temperature of about 250° C. (482° F.) to about 400° C. (752° F.) and a pressure of about 700 kPa (abs) (100 psig) to about 21 MPa (abs) (3000 psig) and preferably about 1.9 MPa (abs) (285 psia) to about 14.7 MPa (abs) (2133 psia). Conditions in the second hydrotreating reactor 22 are operated to achieve a hydrodeoxygenation ratio of greater than that in the first hydrodeoxygenation reactor 16 and/or so as to achieve a hydrodeoxygenation ratio of greater than about 55%, suitably greater than about 60% and preferably at least about 90%.

The hydrodeoxygenated stream in line 26 may be cooled and separated in a first separator 30 to provide a hydrogen gas stream in an overhead line 18 and a liquid hydrodeoxygenated stream in a bottoms line 32. An aqueous stream may be removed from a boot depending from the separator 30. The first separator 30 may be in downstream communication with the hydrodeoxygenation reactor 16 and an unshown upstream hot separator. The first separator 30 may operate at about 30° C. (116° F.) to about 70° C. (158° F.). The first separator 30 may operate at a slightly lower pressure than the hydrodeoxygenation reactor 32 accounting for pressure drop through intervening equipment. The first separator 30 may be operated at pressures between about 1.9 MPa (abs) (285 psia) to about 14.7 MPa (abs) (2133 psia).

The hydrotreated stream in line 28 may be cooled and separated in a second separator 34 to provide a hydrogen gas stream in an overhead line 18 and a liquid hydrodeoxygenated stream in a bottoms line 36. An aqueous stream may be removed from a boot depending from the separator 34. The second separator 34 may be in downstream communication with the hydrotreating reactor 28 and an unshown upstream hot separator. The second separator 34 may operate at about 30° C. (116° F.) to about 70° C. (158° F.). The second separator 34 may operate at a slightly lower pressure than the hydrotreating reactor 22 accounting for pressure drop through intervening equipment. The second separator 34 may be operated at pressures between about 1.9 MPa (abs) (285 psia) to about 14.7 MPa (abs) (2133 psia).

In an embodiment, the first separator 30 and the second separator 34 may be in the same vessel with a baffle isolating the liquid in the first separator from the liquid in the second separator 34. The baffle may have a bottom edge sealed to the bottom of the vessel but a top edge that is spaced apart from the top of the vessel. Consequently, the first separator 30 and the second separator 34 may share the same overhead outlet 24 but have isolated bottom outlets 32 and 36 and isolated boot outlets.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator which may be operated at higher pressure. The term "communication" means that fluid flow is operatively permitted between enumerated components, which may be characterized as "fluid communication". The term "downstream communication" means that at least a portion of fluid flowing to the subject in downstream communication may operatively flow from the object with which it fluidly communicates.

The liquid hydrodeoxygenated stream in line 32 may be fractionated in a splitter column 40 to produce three streams. Alternatively, multiple columns may be employed. The splitter overhead stream is withdrawn from the splitter column 40 in an overhead line, condensed in a cooler and fed to a separator. The condensed overhead stream is recycled to the splitter column 40 as reflux through a reflux line and a net vapor stream comprising C9-hydrocarbons comprising green LPG and naphtha is withdrawn in a net overhead line 42. The green LPG and naphtha may be separated downstream. A liquid side stream is taken from a side 41 of the splitter column 40 in line 44 comprising a light normal paraffin stream in the C10 to C13 carbon range. The composition of the light normal paraffin stream meets applicable detergent alkylation specifications for at least C11 to C13 normal paraffins. The term "Cx" is to be understood to refer to molecules having the number of carbon atoms represented by the subscript "x". Similarly, the term "Cx−" refers to molecules that contain less than or equal to x and preferably x and less carbon atoms. The term "$C_{x+}$" refers to molecules with more than or equal to x and preferably x and more carbon atoms. The light normal paraffin stream in line 44 may be transported to a detergent alkylation unit 200 in FIG. 3.

A splitter bottoms stream is withdrawn from the splitter column 40 through a bottoms line where a portion of the splitter bottoms stream flows through a reboiler line, a reboiler heater and returns heated to the splitter fractionation column 40. The remaining portion of the splitter bottoms stream flows through a net bottoms line 46 comprising a heavy normal paraffin stream in the C14 to C20 carbon range. The splitter fractionation column 40 operates in a bottoms temperature range of about 230 to about 270° C. and an overhead pressure of about 20 kPa to slightly vacuum of about 400 mm Hg (abs). It is envisioned that two fractionation columns could be used to provide the three streams instead of a single column that produces a side stream.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Unless indicated otherwise, overhead lines and bottoms lines refer to the net lines from the column downstream of any reflux or reboil take-off to the column. Stripper columns may omit a reboiler at a bottom of the column and instead provide heating requirements and separation impetus from a fluidized inert media such as steam.

A portion of the hydrotreated stream is mixed with the heavy normal paraffin stream in the net bottoms line 46. Specifically, the liquid hydrotreated stream in the second bottoms line 36 is mixed with the heavy normal paraffin stream in the embodiment of FIG. 1 to provide a hydroisomerization feed stream in line 48. The hydroisomerization feed stream in line 48 may be combined with a recycle stream in line 56 and a hydroisomerization hydrogen stream in line 52 and fed to the hydroisomerization reactor 50. To improve the cold flow properties, the hydroisomerization feed stream may be contacted with a hydroisomerization catalyst in the hydroisomerization reactor 50 under hydroisomerization conditions to hydroisomerize the normal paraffins to branched paraffins.

Hydroisomerization, also known as hydrodewaxing, of normal hydrocarbons in the hydroisomerization reactor 50 can be accomplished over one or more beds of hydroisomerization catalyst, and the hydroisomerization may be operated in a co-current flow mode of operation.

Suitable hydroisomerization catalysts may comprise a metal of Group VIII (IUPAC 8-10) of the Periodic Table and a support material. Suitable Group VIII metals include platinum and palladium, each of which may be used alone or in combination. The support material may be amorphous or crystalline. Suitable support materials include amorphous alumina, amorphous silica-alumina, ferrierite, ALPO-31, SAPO-11, SAPO-31, SAPO-37, SAPO-41, SM-3, MgAPSO-31, FU-9, NU-10, NU-23, ZSM-12, ZSM-22, ZSM-23, ZSM-35, ZSM-48, ZSM-50, ZSM-57, MeAPO-11, MeAPO-31, MeAPO-41, MgAPSO-11, MgAPSO-31, MgAPSO-41, MgAPSO-46, ELAPO-11, ELAPO-31, ELAPO-41, ELAPSO-11, ELAPSO-31, ELAPSO-41, laumontite, cancrinite, offretite, hydrogen form of stillbite, magnesium or calcium form of mordenite, and magnesium or calcium form of partheite, each of which may be used alone or in combination. ALPO-31 is described in U.S. Pat. No. 4,310,440. SAPO-11, SAPO-31, SAPO-37, and SAPO-41 are described in U.S. Pat. No. 4,440,871. SM-3 is described in U.S. Pat. Nos. 4,943,424; 5,087,347; 5,158,665; and 5,208,005. MgAPSO is a MeAPSO, which is an acronym for a metal aluminumsilicophosphate molecular sieve, where the metal, Me, is magnesium (Mg). Suitable MgAPSO-31 catalysts include MgAPSO-31. MeAPSOs are described in U.S. Pat. No. 4,793,984, and MgAPSOs are described in U.S. Pat. No. 4,758,419. MgAPSO-31 is a preferred MgAPSO, where 31 means a MgAPSO having structure type 31. Many natural zeolites, such as ferrierite, that have an initially reduced pore size can be converted to forms suitable for olefin skeletal hydroisomerization by removing associated alkali metal or alkaline earth metal by ammonium ion exchange and calcination to produce the substantially hydrogen form, as taught in U.S. Pat. Nos. 4,795,623 and 4,924,027. Further catalysts and conditions for skeletal hydroisomerization are disclosed in U.S. Pat. Nos. 5,510,306, 5,082,956, and 5,741,759. The hydroisomerization catalyst may also comprise a modifier selected from the group consisting of lanthanum, cerium, praseodymium, neodymium, samarium, gadolinium, terbium, and mixtures thereof, as described in U.S. Pat. Nos. 5,716,897 and 5,851,949. Other suitable support materials include ZSM-22, ZSM-23, and ZSM-35, which are described for use in dewaxing in U.S. Pat. No. 5,246,566 and in the article entitled S. J. Miller, "New Molecular Sieve Process for Lube Dewaxing by Wax Isomerization," 2 Microporous Materials 439-449 (1994). U.S. Pat. Nos. 5,444,032 and 5,608,968 teach a suitable bifunctional catalyst which is constituted by an amorphous silica-alumina gel and one or more metals belonging to Group VIIIA and is effective in the hydroisomerization of long-chain normal paraffins containing more than 15 carbon atoms. U.S. Pat. Nos. 5,981,419 and 5,908,134 teach a suitable bifunctional catalyst which comprises: (a) a porous crystalline material isostructural with beta-zeolite selected from boro-silicate (BOR—B) and boro-alumino-silicate (Al-BOR—B) in which the molar $SiO_2:Al_2O_3$ ratio is higher than 300:1; (b) one or more metal(s) belonging to Group VIIIA, selected from platinum and palladium, in an amount comprised within the range of from 0.05 to 5% by weight. V. Calemma et al., App. Catal. A: Gen., 190 (2000), 207 teaches yet another suitable catalyst. DI-100 available from UOP LLC in Des Plaines, Illinois may be a suitable catalyst.

Hydroisomerization conditions generally include a temperature of about 250° C. (482° F.) to about 400° C. (752° F.) and a pressure of about 1.9 MPa (abs) (285 psia) to about 14.7 MPa (abs) (2133 psia). In another embodiment, the hydroisomerization conditions include a temperature of about 300° C. (572° F.) to about 360° C. (680° F.) and a pressure of about 3102 kPa (abs) (450 psia) to about 6895 kPa (abs) (1000 psia).

A hydroisomerate stream in a hydroisomerate line 54 from the hydroisomerization reactor 50 is a branched-paraffin-rich stream. By the term "rich" it is meant that the effluent stream has a greater concentration of branched paraffins than the stream entering the hydroisomerization reactor 84, and preferably comprises greater than 50 mass-% branched paraffins of the total paraffin content. It is envisioned that the hydroisomerized effluent may contain 70, 80, or 90 mass-% branched paraffins of the total paraffin content.

The hydroisomerate stream in line 54 may be separated in separators that are not shown and stripped of lights in an hydroisomerization stripper 60 to provide a light gaseous stream in an overhead line 62 and a green fuel stream in a bottoms line 64. The hydroisomerization stripper 60 may strip the hydroisomerate stream with steam from line 66 and be operated with a bottoms temperature between about 149° C. (300° F.) and about 288° C. (550° F.) and an overhead pressure of about 0.35 MPa (gauge) (50 psig) to no more than about 2.0 MPa (gauge) (290 psig) just below the pressure of the hydroisomerization reactor 50 accounting for the pressure drop of intervening equipment.

The liquid green fuel stream in line 64 may be dried and fractionated in a product column 70 to produce three streams. The product overhead stream is withdrawn from the product column 70 in an overhead line, fully condensed in a cooler and fed to a separator. A portion of the condensed overhead stream is recycled to the product fractionation column 70 as reflux through a reflux line and a net liquid stream comprising green naphtha is withdrawn in a net overhead liquid line 72. A liquid side stream is taken from a side 71 of the product column 70 in line 74 comprising a paraffin stream in the jet fuel range of an initial boiling point of about 80° C. to about 120° C. and an end point of about 290° C. to about 310° C. As used herein, the term "initial boiling point" (IBP) means the temperature at which the sample begins to boil using ASTM D-86. As used herein, the term "end point" (EP) means the temperature at which the sample has all boiled off using ASTM D-86.

A product bottoms stream is withdrawn from the product column 70 through a bottoms line where a portion of the splitter bottoms stream flows through a reboiler line, a reboiler heater and returns heated to the product fractionation column 70. The remaining portion of the product bottoms stream flows through a net bottoms line 76 comprising green diesel in the C17 to C20 carbon range. A portion or all of the green diesel stream may be recycled in line 56 to be combined with the hydroisomerization feed stream in line 48 and hydroisomerized in the hydroisomerization reactor 50. A portion or all of the green diesel may be recovered in line 78. The product fractionation column 70 operates in a bottoms temperature range of 250° C. (482° F.) and about 350° C. (662° F.) and an overhead pressure of about 200 mm Hg (abs at 0° C.) (3.9 psia) to no more than about 1.0 MPa (abs) (145 psia).

Figure 2:
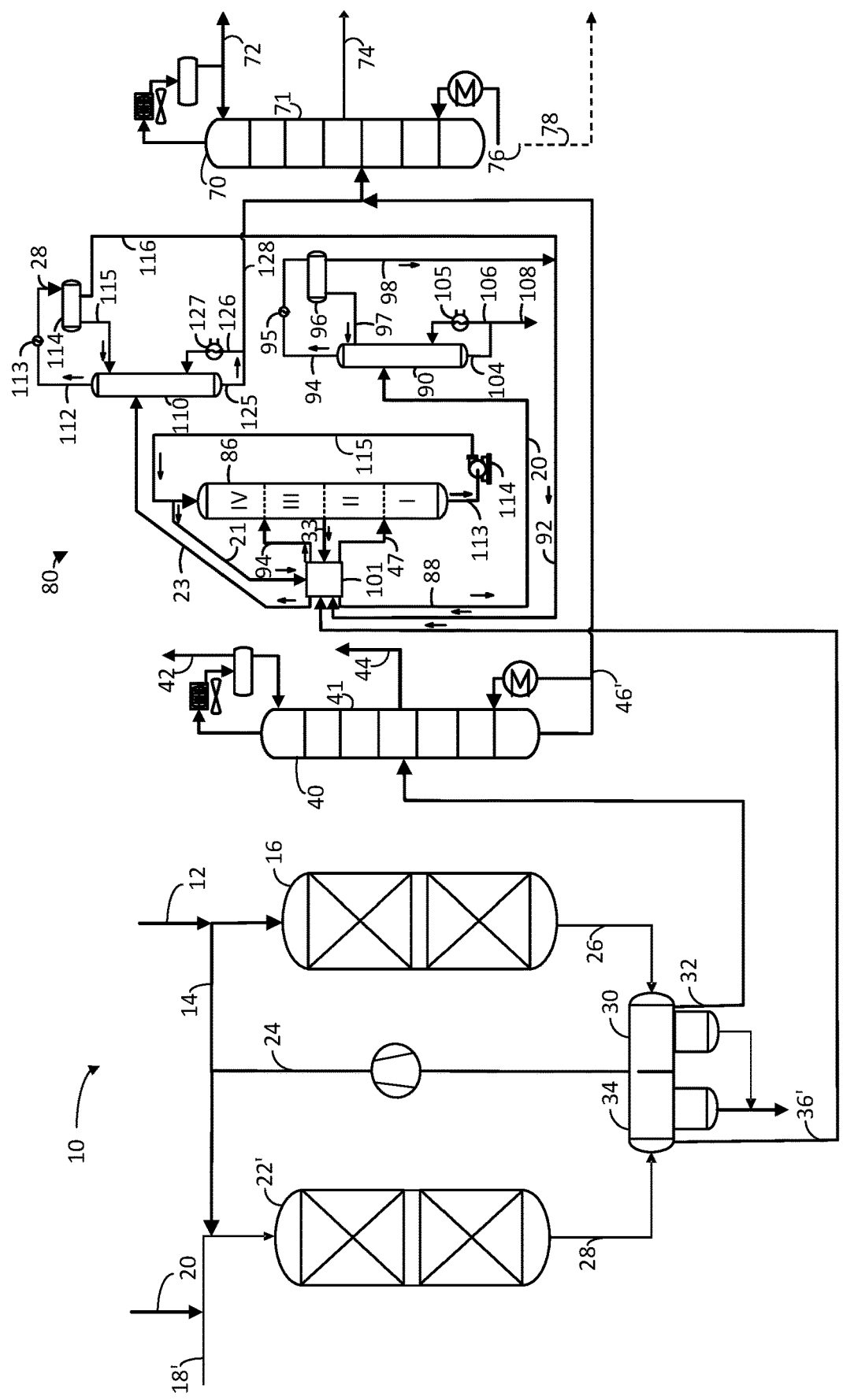
FIG. 2 is a schematic view of an alternate conversion unit of FIG. 1.

FIG. 2 depicts an embodiment in which the second feed stream in line 18' is a mineral oil stream such as kerosene and the second hydrotreating reactor 22' contains hydrotreating catalyst. Many of the elements in FIG. 2 have the same configuration as in FIG. 1 and bear the same reference number. Elements in FIG. 2 that correspond to elements in FIG. 1 but have a different configuration bear the same reference numeral as in FIG. 1 but are marked with a prime symbol (').

The second feed stream in line 18' may be a conventional hydrocarbon feed stream that is extracted from the earth, such as a mineral oil stream. In an embodiment, the hydrocarbon feed stream in line 18' is preferably a kerosene stream. The second feed stream may comprise hydrocarbons boiling in the range of an IBP of between about 70° C. and about 120° C., and an EP between about 280° C. and about 320° C. The first feed stream is hydrodeoxygenated and the hydrodeoxygenated stream is recovered and processed as described for the first embodiment, but the second feed stream is hydrotreated to remove heteroatoms and saturate olefins that may be present in the mineral oil feed stream. The hydrotreated stream in line 28 is fed to a second separator 34 which may be in the same vessel as the first separator 30, but the liquid hydrotreated stream in line 36' may be fed to an adsorption separation unit 80 to separate normal paraffins from iso-paraffins. Normal paraffins are desired for detergent alkylation and the isoparaffins are desired for fuel streams.

Suitable hydrotreating catalysts are any known conventional hydrotreating catalysts and include those which are comprised of at least one Group VIII metal, preferably iron, cobalt and nickel, more preferably cobalt and/or nickel and at least one Group VI metal, preferably molybdenum and tungsten, on a high surface area support material, preferably alumina. Other suitable hydrotreating catalysts include zeolitic catalysts, as well as noble metal catalysts where the noble metal is selected from palladium and platinum. It is within the scope of the present description that more than one type of hydrotreating catalyst be used in the hydrotreating reactor 22'. The Group VIII metal is typically present in an amount ranging from about 2 to about 20 wt %, preferably from about 4 to about 12 wt %. The Group VI metal will typically be present in an amount ranging from about 1 to about 25 wt %, preferably from about 2 to about 25 wt %.

Preferred hydrotreating reaction conditions include a temperature from about 290° C. (550° F.) to about 455° C. (850° F.), suitably 316° C. (600° F.) to about 427° C. (800° F.) and preferably 343° C. (650° F.) to about 399° C. (750° F.), a pressure from about 2.8 MPa (gauge) (400 psig) to about 17.5 MPa (gauge) (2500 psig), a liquid hourly space velocity of the fresh hydrocarbonaceous feedstock from about 0.1 $hr^{-1}$, suitably 0.5 $hr^{-1}$, to about 5 $hr^{-1}$, preferably from about 1.5 to about 4 $hr^{-1}$, and a hydrogen rate of about 84 $Nm^3/m^3$ (500 scf/bbl), to about 1,011 $Nm^3/m^3$ oil (6,000 scf/bbl), preferably about 168 $Nm^3/m^3$ oil (1,000 scf/bbl) to about 1,250 $Nm^3/m^3$ oil (7,500 scf/bbl), with a hydrotreating catalyst or a combination of hydrotreating catalysts.

The liquid hydrotreated stream in line 36' is passed to an adsorbent separation unit 80. The feed stream in feed line 36' is passed through a valve 101 in the adsorbent separation unit 80 which delivers the feed to an appropriate bed in an adsorbent vessel 86.

The liquid hydrodeoxygenated stream in line 32 is fractionated in the splitter column 40 as in the embodiment of FIG. 1. The heavy normal paraffin stream in the net bottoms line 46' is fed to the product column with a raffinate bottoms stream in a net bottoms line 128 to be fractionated into fuel streams.

As used herein, the term "a component-rich stream" or "a component stream" means that the stream coming out of a vessel has a greater concentration of the component than the feed to the vessel. As used herein, the term "a component-lean stream" means that the lean stream coming out of a vessel has a smaller concentration of the component than the feed to the vessel.

In the adsorbent separation unit 80, the liquid hydrotreated stream in line 36' is separated into a normal paraffins stream and an isoparaffins stream. Normal paraffins in the liquid hydrotreated stream selectively enter or occlude into the porous structure of the adsorbent components but branched hydrocarbons do not typically enter the pores. The isoparaffins exit the process as a raffinate stream. To provide a useful method for separation of normal from iso-paraffins, it is necessary to desorb the occluded normal paraffins. In the disclosed process, iso or normal pentane, hexane, heptane or octane and mixtures thereof can suitably be used as a desorbent to desorb normal paraffins in an extract-desorbent stream.

The adsorbent used in the adsorbent vessel preferably comprises aluminosilicate molecular sieves having relatively uniform pore diameters of about 5 Angstroms. The preferred adsorbent is provided by commercially available type 5A molecular sieves produced and sold by UOP LLC in Des Plaines, Illinois.

The adsorbent vessel 86 may comprise a series of vertically spaced, separate beds interconnected by a pipe 115 between the bottom of one bed and the top of its downstream adjacent bed. The valve 101 may comprise a manifold arrangement or a rotary valve for advancing the points of inlet and outlet of respective streams in a downstream direction. The adsorbent vessel 86 operates in a downflow mode, although upflow may be suitable. The adsorbent vessel 86 is shown to have four main zones I-IV for simplicity, though these zones may be further subdivided when accounting for different flushing schemes. The overall process may have other numbers of beds, such as eight, twelve or twenty-four beds, divided among the four main zones I-IV.

The hydrotreated stream is introduced through line 36' through valve 101 which is positioned to send the feed stream through line 47 into the adsorbent vessel 86 between Zones I and II. The extract is withdrawn between Zones II and III in line 33, transported through the valve 101 in an extract line 88 to an extract fractionation column 90 to separate desorbent from extract. The desorbent is introduced through desorbent line 92 through the valve 101 which is positioned to send the desorbent through a desorbent line 94 into the process between Zones III and IV. The raffinate is withdrawn between Zones IV and I through a raffinate line 21, through the valve 101 and through line 23 to the raffinate fractionation column 110.

Simulated countercurrent flow is achieved by periodically advancing downstream the introduction point of the feed stream and the desorbent stream while simultaneously and equally advancing downstream the withdrawal point of the raffinate stream and the extract stream. The Zone I is defined as the zone bounded between the feed stream inlet and the raffinate outlet; the Zone II is defined as the zone bounded between the extract stream outlet and the desorbent inlet; the Zone III is defined as the zone bounded between the desorbent inlet and the extract outlet; and the Zone IV is defined as the zone bounded between the raffinate stream outlet and the desorbent stream inlet. Typical liquid phase operation is preferred, for example, at temperatures from about 50° C. to about 300° C., and more particularly no more than about 260° C., and pressures from slightly super atmospheric to about 30 atmospheres.

Raffinate, characterized as comprising molecules less adsorbed in the adsorbent vessel 86, is withdrawn from the adsorbent vessel in the raffinate line 21 through the valve 101 and enters the raffinate fractionation column 110 through line 23. Since it is desired to obtain a normal paraffin product, the raffinate fractionation column 24 is operated to separate two fractions, a raffinate bottoms stream rich in iso-paraffins, in an embodiment, rich in C10 to C14 iso-paraffins, and a desorbent bottoms stream rich in lighter paraffin desorbent, in an embodiment, rich in C5 or C6 normal paraffins. The desorbent overhead bottoms stream is withdrawn from the raffinate fractionation column 110 in an overhead line 112, condensed in a cooler 113 and fed to a separator 114. A portion of the condensed raffinate overhead is recycled to the raffinate fractionation column 110 as reflux through a reflux line 115 and the remaining portion of the condensed raffinate overhead is withdrawn through a net raffinate overhead line 116. The net raffinate overhead stream is rich in normal pentane or hexane desorbent which can join the extract desorbent stream in line 98. Both can be recycled in the desorbent line 92 through the valve 101 to the adsorbent vessel 86 in the desorbent line 94.

The raffinate bottoms stream is withdrawn from the raffinate fractionation column 110 through a bottoms line 125 where a portion of the raffinate bottoms stream flows through a reboiler line 126, reboiler heater 127 and returns heated to the raffinate fractionation column 110. The remaining portion of the raffinate bottoms stream flows through a net bottoms line 128 as an isoparaffin rich stream, particularly rich in C10-C14 isoparaffins. Because the raffinate bottoms stream is rich in isoparaffins, it will make an excellent fuel feed stock and is fed to the product column 70. The raffinate fractionation column 110 operates in a bottoms temperature range of about 200 to about 280° C. and an overhead pressure of around atmospheric.

The extract stream comprises molecules more selectively adsorbed on the adsorbent in the adsorbent vessel 86. The desorbent displaces the selectively adsorbed normal paraffins from the solid adsorbent in desorbent bed III of adsorbent vessel 86. The extract and desorbent are withdrawn in line 33, and the valve 101 connects line 33 with line 88. Extract and desorbent withdrawn from the adsorbent vessel in the extract line 33 connected through the valve 101 is directed in line 88 to the extract fractionation column 90. Since it is desired to obtain a normal paraffin product, the extract fractionation column 90 is operated to separate two fractions, an extract overhead stream rich in normal paraffins, in an embodiment, rich in normal pentane or hexane desorbent and a bottoms stream rich in normal paraffin extract, in an embodiment, rich in C10-C14 normal paraffins. The desorbent overhead stream is withdrawn from the extract fractionation column 90 in an overhead line 94, condensed in a cooler 95 and fed to a separator 96. A portion of the condensed desorbent overhead stream is recycled to the extract fractionation column 90 as reflux through a reflux line 97 and the remaining portion of the condensed desorbent overhead stream is withdrawn through a net desorbent extract overhead line 98. The desorbent overhead stream is rich in normal pentane or hexane desorbent which can join the raffinate desorbent stream in line 116 comprising a raffinate desorbent stream. Both can be recycled in the desorbent line 92 through the valve 101 to the adsorbent vessel 86 in the desorbent line 94.

The extract bottoms stream is withdrawn from extract fractionation column 90 through a bottoms line 104 where a portion of the extract bottoms stream flows through a reboiler line 106, reboiler heater 105 and returns heated to the extract fractionation column 90. A remaining portion of the extract bottoms stream flows through line 108 as a normal paraffin rich stream, particularly rich in normal C10-C14 paraffins. The extract fractionation column 90 operates in bottoms temperature range of about 200 to about 280° C. and an overhead pressure of about atmospheric.

Figure 3:
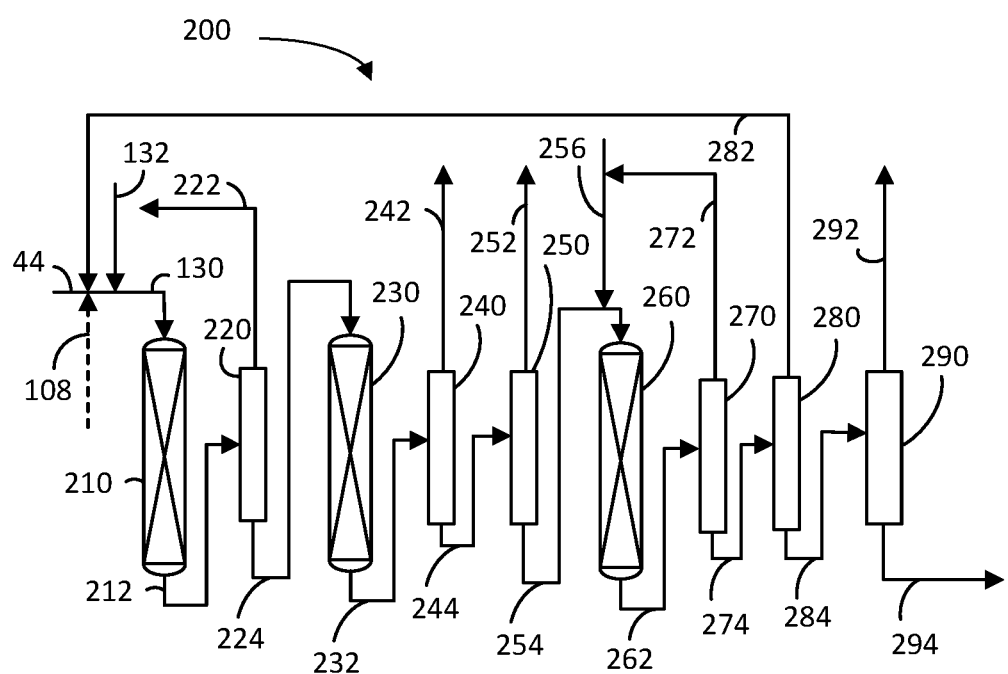
FIG. 3 is a schematic view of a benzene alkylation unit useful with the conversion unit of either FIG. 1 or FIG. 2.

The extract bottoms stream in an extract bottoms line 108 is comprises a substantial concentration of normal paraffins which can be transported to a detergent alkylation unit in FIG. 3 along with the light normal paraffin stream in the side line 44 from the splitter column 40.

FIG. 3 depicts the alkylbenzene unit 200 to which the liquid side stream from a side 41 of the splitter column 40 in line 44 comprising the light normal paraffin stream in the C10 to C13 carbon range from FIGS. 1 and 2 and/or the extract bottoms stream comprising a substantial concentration of normal paraffins in the extract bottoms line 108 from FIG. 2 may be fed in line 130.

As shown in FIG. 3, the light normal paraffin stream in the C10 to C13 carbon range from line 44 and perhaps line 108 is introduced to the alkylbenzene unit 200 after mixing with a recycle paraffins stream in line 282. The light normal paraffin streams in lines 44 and 108 may also be supplemented with a normal decane stream in line 132 to meet detergent alkylation specifications and a combined light normal paraffin stream in line 130 may be fed to the dehydrogenation reactor 210 in the alkylbenzene unit 200. In the dehydrogenation reactor 210, the light paraffins in line 130 are dehydrogenated into mono-olefins of the same carbon numbers as in the light normal paraffin stream. Typically, dehydrogenation occurs through known catalytic processes, such as the commercially popular Pacol Process available from UOP LLC in Des Plaines, Illinois Di-olefins (i.e., dienes) and aromatics are also produced as an undesired result of the dehydrogenation reactions as expressed in the following equations:

Mono-olefin formation: $C_XH_{2X+2} \rightarrow C_XH_{2X} + H_2$ 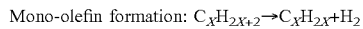

Di-olefin formation: $C_XH_{2X} \rightarrow C_XH_{2X-3} + H_2$ 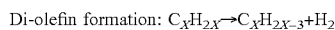

Aromatic formation: $C_XH_{2X-2} \rightarrow C_XH_{2X-6} + 2H_2$ 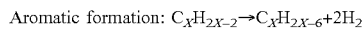

Operating conditions for the dehydrogenation reactor 210 include space velocities from about 5 to about 50 LHSV and from about 20 to about 32 LHSV; pressures from about 35 kPa (5 psig) to about 350 kPa (50 psig) and from about 105 kPa (15 psig); to about 175 kPa (25 psig); temperatures from about 400 to about 500° C. and from about 440 to about 490° C., and hydrogen to hydrocarbon mole ratios from about 1 to about 12 and from about 3 to about 7. An example of a suitable catalyst is a platinum on alumina catalyst where platinum is attenuated with an attenuator metal. Another suitable catalyst is described in U.S. Pat. No. 6,177,381. The unit may be operated dry or with water injection up to about 2000 mass-ppm water.

In FIG. 3, a dehydrogenated light normal olefin stream 212 exits the dehydrogenation reactor 210 comprising mono-olefins and hydrogen, as well as some di-olefins and aromatics. The dehydrogenated stream in line 212 is delivered to a separator 220 for removing the hydrogen from the dehydrogenated light normal olefin stream in line 212. As shown, the hydrogen exits the separator 220 in a recycle stream of hydrogen 222 that can be recycled to line 20 in FIG. 1 or FIG. 2 to support the hydrodeoxygenation or hydrotreating processes upstream.

The separator 220 produces a dehydrogenated liquid light normal olefin stream in a bottoms line 224 comprising the mono-olefins and any di-olefins and aromatics formed during dehydrogenation. The dehydrogenated liquid light normal olefin stream 224 exits the separator 220 and enters a selective hydrogenation reactor 230, such as a DeFine reactor available from UOP, LLC. The selective hydrogenation reactor 230 selectively hydrogenates at least a portion of the di-olefins in the dehydrogenated liquid light normal olefin stream 224 to form additional mono-olefins. As a result, a selectively dehydrogenated light normal olefin stream 232 is formed with an increased mono-olefin concentration.

As shown, the selectively dehydrogenated stream 232 passes from the selective hydrogenation reactor 230 to a lights separator 240, such as a stripper column, which removes a light end stream in an overhead line 242 containing any lights, such as butane, propane, ethane and methane, that resulted from cracking or other reactions during upstream processing. With the light ends removed, a de-lighted light normal olefin stream in a bottoms line 244 may be delivered to an aromatic removal unit 250, such as a Pacol Enhancement Process available from UOP, LLC. The aromatic removal unit 250 removes aromatics in line 252 from the de-lighted light normal olefin stream in bottoms line 244 perhaps by contact with a solvent to produce a dearomaticized, light normal olefin stream in the C10-C13 range in line 254.

The stream of light normal olefins in line 254 and a stream of benzene 256 are fed into an alkylation unit 260. The alkylation unit 260 holds a catalyst, such as a solid acid catalyst, that supports alkylation of the benzene with the mono-olefins. Fluorided silica-alumina, hydrogen fluoride (HF), aluminum chloride (AlCl3), and zeolitic catalysts are examples of major catalysts in commercial use for the alkylation of benzene with linear mono-olefins and may be used in the alkylation unit 260. As a result of alkylation, alkylbenzene, typically called linear alkylbenzene (LAB), is formed according to the reaction:

$C_6H_6 + C_XH_{2X} \rightarrow C_6H_5C_XH_{2X+1}$ 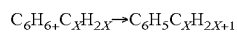

and are present in an alkylation effluent in line 262.

Suitable operating conditions for the alkylation unit include space velocities from 1 to about 10 LHSV, pressures to maintain liquid phase operation such as about 2.1 MPa (300 psig) to about 4.2 MPa (600 psig), temperatures in the range of from about 80° C. to about 180° C. and preferably 120° C. to about 170° C., and benzene-to-olefin mole ratios of about 3 to about 40 and preferably about 8 to about 35.

Surplus amounts of benzene in line 256 are supplied to the alkylation unit 260 to achieve high degree of desired alkylation. Therefore, the alkylation effluent 262 exiting the alkylation unit 260 contains alkylbenzene and unreacted benzene. Further the alkylation effluent in line 262 may also include some unreacted paraffins. The alkylation effluent in line 262 is passed to a benzene separation unit 270, such as a fractionation column, for separating the unreacted benzene from the alkylation effluent. This unreacted benzene exits the benzene separation unit 270 in a benzene recycle stream 272 that is delivered back into the alkylation unit 260 in the benzene line 256 to reduce the volume of fresh benzene required therein.

As shown, a benzene-stripped stream exits the benzene separation unit 270 in line 274 and enters a paraffinic separation unit 280, such as a fractionation column. In the paraffinic separation unit 280, unreacted paraffins are removed from the benzene-stripped stream 274 in a recycle paraffin stream in line 282 and are routed to and mixed with the light normal paraffin stream in line 44 and the extract bottoms stream in the extract bottoms line 108 to provide the light normal paraffin stream in line 130 for dehydrogenation as described above. Further, an alkylbenzene stream 284 is separated by the paraffinic separation unit 280 and is fed to an alkylate separation unit 290. The alkylate separation unit 290, which may be, for example, a multi-column fractionation unit, separates a heavy alkylate bottoms stream 294 from an alkylbenzene product stream in line 292.

As a result of the post-alkylation separation processes, the linear alkylbenzene product in line 292 is isolated and exits the alkylbenzene unit 200.

By hydrodeoxygenating a biorenewable feed that is concentrated in free fatty acids with 12 and 14 carbon atoms at a moderate hydrodeoxygenation ratio which is less than the ratio of hydrodeoxygenation utilized for traditional biorenewable feeds such as vegetable oil or even mineral feedstocks, normal paraffins in the range desired by the detergents industry can be produced. Either hydroisomerization or an iso-normal separation can be performed to generate green fuel streams.

Example

We charged a feed of PKO to a hydrodeoxygenation pilot plant operated at hydrodeoxygenation ratios shown in Table 1. Hydrodeoxygenation ratios were adjusted by tuning the catalyst and selecting the reaction temperature.

TABLE 1

| % HDO | 92% | 75% | 60% | 55% | 50% | 40% | 35% | 30% |
|---|---|---|---|---|---|---|---|---|
| nC10 | 6.7 | 5.2 | 4.0 | 3.6 | 3.2 | 2.5 | 2.2 | 1.8 |
| nC11 | 6.6 | 19.8 | 30.4 | 33.7 | 37.0 | 43.3 | 46.3 | 49.2 |
| nC12 | 83.2 | 64.6 | 49.6 | 44.9 | 40.3 | 31.4 | 27.2 | 23.0 |
| nC13 | 3.5 | 10.4 | 16.0 | 17.8 | 19.5 | 22.8 | 24.4 | 26.0 |
| Avg. Mol. Wt. | 167.3 | 166.7 | 166.2 | 166.0 | 165.9 | 165.6 | 165.5 | 165.4 |

Hydrodeoxygenation ratios of 40, 50 and 55% in the pilot plant provided nC11-13 selectivities and molecular weight in the ranges specified by an exemplary detergent manufacturer in Table 2.

TABLE 2

| Component | Range, wt % |
|---|---|
| C10 | 13.5-22 |
| C11 | 29.6-44.5 |
| C12 | 25.5-45.7 |
| C13 | 10.5-31 |
| Isoparaffins | <1.5 |
| Avg. Mol. Wt. | 160-164 |

To meet the specifications of an exemplary detergent manufacturer, we added normal C10 to generate nC10-13 in the specified weight ranges of Table 2 as shown in Table 3.

TABLE 3

| % HDO | 55% | 50% | 40% |
|---|---|---|---|
| nC10 | 13.5 | 13.6 | 13.7 |
| nC11 | 30.2 | 33.0 | 38.3 |
| nC12 | 40.3 | 36.0 | 27.8 |
| nC13 | 16.0 | 17.4 | 20.2 |
| Avg. Mol. Wt. | 163.2 | 163.0 | 162.5 |

Isoparaffins were produced below the 1.5 wt % maximum, and the resulting average molecular weight met the detergent specification of Table 2. By operating the hydrodeoxygenation reaction to achieve desired hydrodeoxygenation ratios, appropriate biorenewable feeds can be hydrodeoxygenated to desired selectivities, particularly to meet detergent manufacturing specifications.

Specific Embodiments

While the following is described in conjunction with specific embodiments, it will be understood that this description is intended to illustrate and not limit the scope of the preceding description and the appended claims.

A first embodiment of the invention is a process for hydroprocessing two feed streams comprising hydrodeoxygenating a biorenewable feed stream in the presence of hydrogen and a hydrodeoxygenation catalyst to produce a hydrodeoxygenated stream; hydrotreating a second feed stream in the presence of hydrogen and a hydrotreating catalyst to provide a hydrotreated stream; fractionating the hydrodeoxygenated stream to provide a light normal paraffin stream and a heavy normal paraffin stream; and mixing a portion of the hydrotreated stream with the light normal paraffin stream or the heavy normal paraffin stream. An embodiment of the invention is one, any or all of prior embodiments in this paragraph up through the first embodiment in this paragraph wherein the heavy normal paraffin stream is mixed with a liquid hydrotreated stream to provide an isomerization feed stream and hydroisomerizing the hydroisomerization feed stream in the presence of hydrogen and a hydroisomerization catalyst to produce an hydroisomerate stream. An embodiment of the invention is one, any or all of prior embodiments in this paragraph up through the first embodiment in this paragraph further comprising dehydrogenating the light normal paraffin stream to produce a light normal olefin stream and alkylating the light normal olefin stream with a benzene stream to produce an alkylbenzene stream. An embodiment of the invention is one, any or all of prior embodiments in this paragraph up through the first embodiment in this paragraph wherein the biorenewable feed stream is concentrated in free fatty acids having 12 and 14 carbon atoms. An embodiment of the invention is one, any or all of prior embodiments in this paragraph up through the first embodiment in this paragraph further wherein the second feed stream is a biorenewable feed stream comprising conventional biorenewable oil. An embodiment of the invention is one, any or all of prior embodiments in this paragraph up through the first embodiment in this paragraph further comprising separating a normal paraffin rich stream from a liquid hydrotreated stream; mixing the normal paraffin rich stream with the light normal paraffin stream; dehydrogenating the light normal paraffin stream to produce a light normal olefin stream and alkylating the light normal olefin stream with a benzene stream to produce an alkylbenzene stream. An embodiment of the invention is one, any or all of prior embodiments in this paragraph up through the first embodiment in this paragraph wherein the second feed stream is a kerosene feed stream. An embodiment of the invention is one, any or all of prior embodiments in this paragraph up through the first embodiment in this paragraph further comprising operating the hydrodeoxygenation step at a hydrodeoxygenation ratio of about 35 to about 60%. An embodiment of the invention is one, any or all of prior embodiments in this paragraph up through the first embodiment in this paragraph further comprising operating the hydrotreating step at a hydrodeoxygenation ratio of greater than in the hydrodeoxygenation step. An embodiment of the invention is one, any or all of prior embodiments in this paragraph up through the first embodiment in this paragraph further comprising separating the hydroisomerate stream into naphtha and jet fuel.

A second embodiment of the invention is a process for hydrodeoxygenating two feed streams comprising hydrodeoxygenating a biorenewable feed stream in the presence of hydrogen and a first hydrodeoxygenation catalyst to produce a first hydrodeoxygenated stream; hydrodeoxygenating a second feed stream in the presence of hydrogen and a second hydrodeoxygenation catalyst to provide a second hydrodeoxygenated stream; fractionating the first hydrodeoxygenated stream to provide a light normal paraffin stream and a heavy normal paraffin stream; and mixing a portion of the second hydrodeoxygenated stream with the light normal paraffin stream or the heavy normal paraffin stream. An embodiment of the invention is one, any or all of prior embodiments in this paragraph up through the second embodiment in this paragraph wherein the first hydrodeoxygenating step is run at a different hydrodeoxygenating ratio than the second hydrodeoxygenating step. An embodiment of the invention is one, any or all of prior embodiments in this paragraph up through the second embodiment in this paragraph further comprising mixing the heavy normal paraffin stream with a liquid second hydrodeoxygenated stream to provide an hydroisomerization feed stream and hydroisomerizing the hydroisomerization feed stream in the presence of hydrogen and hydroisomerization catalyst to produce an hydroisomerate stream. An embodiment of the invention is one, any or all of prior embodiments in this paragraph up through the second embodiment in this paragraph further comprising dehydrogenating the light normal paraffin stream to produce a light normal olefin stream and alkylating the light normal olefin stream with a benzene stream to produce an alkylbenzene stream. An embodiment of the invention is one, any or all of prior embodiments in this paragraph up through the second embodiment in this paragraph wherein the biorenewable feed stream is concentrated in hydrocarbons having 12 and 14 carbon atoms. An embodiment of the invention is one, any or all of prior embodiments in this paragraph up through the second embodiment in this paragraph further wherein the second feed stream is a biorenewable feed stream comprising conventional vegetable oil.

A third embodiment of the invention is a process for producing alkylbenzene from a renewable feedstock comprising hydrodeoxygenating a biorenewable feed stream in the presence of hydrogen and a first hydrodeoxygenation catalyst at a first hydrodeoxygenation ratio to produce a first hydrodeoxygenated stream; hydrodeoxygenating a second feed stream in the presence of hydrogen and a second hydrodeoxygenation catalyst at a second hydrodeoxygenation ratio to produce a second hydrodeoxygenated stream; and mixing at least a portion of the first hydrodeoxygenated stream with at least a portion of the second hydrodeoxygenated stream. An embodiment of the invention is one, any or all of prior embodiments in this paragraph up through the third embodiment in this paragraph further comprising fractionating the first hydrodeoxygenated stream to provide a light normal paraffin stream and a heavy normal paraffin stream and dehydrogenating the light normal paraffin stream to produce a light normal olefin stream and alkylating the light normal olefin stream with a benzene stream to produce an alkylbenzene stream. An embodiment of the invention is one, any or all of prior embodiments in this paragraph up through the third embodiment in this paragraph further comprising mixing a liquid second hydrodeoxygenated stream taken from the second hydrodeoxygenated stream with the heavy normal paraffin stream to provide an hydroisomerization feed stream and hydroisomerizing the hydroisomerization feed stream in the presence of hydrogen and hydroisomerization catalyst to produce an hydroisomerate stream and separating the hydroisomerate stream into naphtha and jet fuel or diesel. An embodiment of the invention is one, any or all of prior embodiments in this paragraph up through the third embodiment in this paragraph further comprising operating the first hydrodeoxygenation step at a hydrodeoxygenation ratio of about 35 to about 60%.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for hydroprocessing two feed streams comprising:
   hydrodeoxygenating a biorenewable feed stream in the presence of hydrogen and a hydrodeoxygenation catalyst to produce a hydrodeoxygenated stream, wherein said biorenewable feed stream comprises at least 30 wt % free fatty acids having 12 and 14 carbon atoms;
   hydrotreating a second feed stream comprising free fatty acids in the presence of hydrogen and a hydrotreating catalyst to provide a hydrotreated stream, wherein said second feed stream comprises less than 30 wt % free fatty acids having 12 and 14 carbon atoms;
   operating the hydrotreating step at a greater hydrodeoxygenation ratio than the hydrodeoxygenation step, wherein the hydrodeoxygenation ratio is the proportion of mass flow rate of normal paraffins with even carbon number to mass flow rate of normal paraffins in hydrodeoxygenation reaction product;
   fractionating the hydrodeoxygenated stream to provide a light normal paraffin stream and a heavy normal paraffin stream; and
   mixing a portion of the hydrotreated stream with the light normal paraffin stream or the heavy normal paraffin stream.

2. The process of claim 1 wherein said heavy normal paraffin stream is mixed with a liquid hydrotreated stream taken from said hydrotreated stream to provide an isomerization feed stream and hydroisomerizing said isomerization feed stream in the presence of hydrogen and a hydroisomerization catalyst to produce an isomerate stream.

3. The process of claim 2 further comprising dehydrogenating said light normal paraffin stream to produce a light normal olefin stream and alkylating said light normal olefin stream with a benzene stream to produce an alkylbenzene stream.

4. The process of claim 2 further comprising separating said isomerate stream into naphtha and jet fuel.

5. The process of claim 1 further comprising separating a normal paraffin rich stream from a liquid hydrotreated stream taken from said hydrotreated stream; mixing said normal paraffin rich stream with said light normal paraffin stream; dehydrogenating said light normal paraffin stream to produce a light normal olefin stream and alkylating said light normal olefin stream with a benzene stream to produce an alkylbenzene stream.

6. The process of claim 1 further comprising operating the hydrodeoxygenation step at a hydrodeoxygenation ratio of about 35 to about 60%.

7. A process for hydrodeoxygenating two feed streams comprising:
   hydrodeoxygenating a first biorenewable feed stream selected from palm kernel oil, coconut oil and babassu oil in the presence of hydrogen and a first hydrodeoxygenation catalyst to produce a first hydrodeoxygenated stream;
   hydrodeoxygenating a second biorenewable feed stream in the presence of hydrogen and a second hydrodeoxygenation catalyst to provide a second hydrodeoxygenated stream, wherein the second biorenewable feed stream comprises less than 30 wt % free fatty acids having 12 and 14 carbon atoms, operating the hydrodeoxygenation of the second biorenewable feed stream at a greater hydrodeoxygenation ratio than the hydrodeoxygenation of the first biorenewable feed stream, wherein the hydrodeoxygenation ratio is the proportion of mass flow rate of normal paraffins with even carbon number to mass flow rate of normal paraffins in hydrodeoxygenation reaction product;

fractionating the first hydrodeoxygenated stream to provide a light normal paraffin stream and a heavy normal paraffin stream; and mixing a portion of the second hydrodeoxygenated stream with the light normal paraffin stream or the heavy normal paraffin stream.

8. The process of claim 7 further comprising mixing said heavy normal paraffin stream with a liquid second hydrodeoxygenated stream taken from said second hydrodeoxygenated stream to provide an isomerization feed stream and hydroisomerizing said isomerization feed stream in the presence of hydrogen and hydroisomerization catalyst to produce an isomerate stream.

9. The process of claim 8 further comprising dehydrogenating said light normal paraffin stream to produce a light normal olefin stream and alkylating said light normal olefin stream with a benzene stream to produce an alkylbenzene stream.

10. The process of claim 9 wherein said first biorenewable feed stream is concentrated in hydrocarbons having 10 to 14 carbon atoms.

* * * * *